US010993950B2

(12) United States Patent
Poli

(10) Patent No.: US 10,993,950 B2
(45) Date of Patent: May 4, 2021

(54) MEDICAL DEVICE FOR THE TREATMENT OF HPV CUTANEOUS INFECTIONS

(71) Applicant: Poli MD S.R.L., Rome (IT)

(72) Inventor: Elena Poli, Rome (IT)

(73) Assignee: Poli MD S.R.L., Rome (IT)

( * ) Notice: Subject to any disclaimer, the term of this patent is extended or adjusted under 35 U.S.C. 154(b) by 0 days.

(21) Appl. No.: 16/476,995

(22) PCT Filed: Jul. 11, 2018

(86) PCT No.: PCT/IB2018/055092
§ 371 (c)(1),
(2) Date: Jul. 10, 2019

(87) PCT Pub. No.: WO2019/025884
PCT Pub. Date: Feb. 7, 2019

(65) Prior Publication Data
US 2019/0350946 A1    Nov. 21, 2019

(30) Foreign Application Priority Data

Aug. 4, 2017  (IT) .................. 102017000090344
Jun. 21, 2018  (IT) .................. 102018000006535

(51) Int. Cl.
*A61K 31/616*    (2006.01)
*A61K 9/00*    (2006.01)
(Continued)

(52) U.S. Cl.
CPC ............ *A61K 31/616* (2013.01); *A61B 17/32* (2013.01); *A61K 9/0014* (2013.01);
(Continued)

(58) Field of Classification Search
None
See application file for complete search history.

(56) References Cited

U.S. PATENT DOCUMENTS 2,990,328 A * 6/1961 Lincoln ................ A61K 47/183
514/163
6,703,009 B1 * 3/2004 Rosen .................... A61K 8/342
424/73
(Continued)

FOREIGN PATENT DOCUMENTS

WO    2011076401 A1    6/2011
WO    2017037684 A1    3/2017
WO    WO-2017037684 A1 *  3/2017 ......... A61K 2300/00

OTHER PUBLICATIONS

Pharmacy:Collodions; Dec. 24, 2014 (Year: 2014).*
PCT International Search Report, Application No. PCT/IB2018/055092, dated Oct. 8, 2018.

*Primary Examiner* — Melissa S Mercier
(74) *Attorney, Agent, or Firm* — MacMillan, Sobanski & Todd, LLC

(57) ABSTRACT

The present invention relates to a medical device for treating papilloma virus (HPV) cutaneous infections, in particular for the treatment of warts and related pathologies. In particular, the present invention relates to a collodion-based composition, particularly elastic collodion, containing acetylsalicylic acid and a composition containing acetylsalicylic acid and a glycol. Such compositions can be used in the treatment of HPV cutaneous infections, in particular benign infections such as warts, papillomas and condylomas.

15 Claims, 5 Drawing Sheets

"Controllo negativo" = Negative control

"Collodio ASA" = Collodion ASA

(51) Int. Cl.
  *A61K 9/06*   (2006.01)
  *A61K 47/10*  (2017.01)
  *A61B 17/32*  (2006.01)
  *A61K 47/32*  (2006.01)
  *A61K 47/38*  (2006.01)
  *A61K 47/44*  (2017.01)
  *A61K 45/06*  (2006.01)

(52) U.S. Cl.
  CPC .............. *A61K 9/0034* (2013.01); *A61K 9/06* (2013.01); *A61K 47/10* (2013.01); *A61K 47/32* (2013.01); *A61K 47/38* (2013.01); *A61K 47/44* (2013.01); *A61B 2017/320004* (2013.01); *A61K 45/06* (2013.01)

(56) References Cited

U.S. PATENT DOCUMENTS

| | | | |
|---|---|---|---|
| 8,709,501 B1 * | 4/2014 | Jansen | ................ A61K 33/04 424/714 |
| 2008/0312196 A1 | 12/2008 | Cohen | |

* cited by examiner

"Controllo negativo" = Negative control

"Collodio ASA" = Collodion ASA

"Controllo negativo" = Negative control

"Collodio ASA" = Collodion ASA

"Primo strato corneo" = First corneum layer

"Strato granuloso" = Granulose layer

"Strato basale" = Basal layer

MEDICAL DEVICE FOR THE TREATMENT OF HPV CUTANEOUS INFECTIONS

This is a national stage application filed under 35 U.S.C. § 371 of international application PCT/IB2018/055092, filed under the authority of the Patent Cooperation Treaty on Jul. 11, 2018, published; which claims the benefit of Italy Patent Application No. 102017000090344, filed on Aug. 4, 2017, and Italy Patent Application No. 102018000006535, filed on Jun. 21, 2018. The entire disclosures of all the aforementioned applications are expressly incorporated herein by reference for all purposes.

TECHNICAL FIELD OF THE INVENTION

The present invention relates to a medical device for the treatment of cutaneous infections from papilloma virus (HPV), in particular for the treatment of warts and related diseases.

BACKGROUND ART

Human papillomaviruses (HPVs) are small DNA viruses of the papovavirus family. Although not capsulated, HPVs are very resistant viruses, with a diameter of about 55 nm. Their genome consists of a circular double chain DNA containing about 8000 pairs of nucleotide bases, associated with histones to form structures similar to small chromosomal entities.

According to their trophism, HPVs can be classified into cutaneous and mucosal. Among the cutaneous types, there are those commonly found in the population (HPV 1, and 4) and those associated with verruciform epidermodysplasia, among which the most important are HPV 5 and HPV 8 due to the high tendency to malignant transformation. Mucosal types are generally divided into high- and low-risk types. Low-risk types (HPV 6 and 11) are almost always absent in invasive squamous cell carcinomas, where high-risk types are always present (HPV 16 and 18).

Benign HPV cutaneous infections are generally classified as warts, papillomas, and condylomas. Papillomas affect the oral cavity, while condylomas affect the genital organs of both men and women.

The wart is a cutaneous formation induced by the human papilloma virus (HPV) and is a benign manifestation consisting of a core of internal tissue fed by blood vessels and lined with layers of epithelial tissue. The virus penetrates the epidermis, infecting it.

The appearance of the wart varies depending on the site where it occurs and on the viral strain causing it. Warts are divided into:

1. Common warts: the cutaneous lesions triggered by the Papilloma virus generally have an irregular shape and develop often (but not always) in an asymptomatic way.

2. Plantar warts: typical of the foot sole, these HPV virus-caused warty lesions are easily transmitted in swimming pools and gyms.

3. Flat warts: raised wart lesions; Papilloma virus, infecting hands, feet, face and legs can cause these cutaneous damages, fading in a short time.

Common warts have a typical rough surface, often creped and unsightly, and normally appear on hands, elbows and knees.

Warts are a fairly common problem: it is estimated that they affect about 10% of the global population, with a tendency to increase. The most affected population group includes school-age children, young people and young adults. The peak is reached in the group aged between 10 and 15 years.

Warts are often asymptomatic and tend to disappear even if not treated, but the healing times are very long, even several years. Given the unsightly appearance of such cutaneous manifestations, affected individuals often resort to treatments for their elimination.

The currently used treatments include:
- surgical removal: it consists of total removal of the infected skin area. Although this method is effective, it is very invasive and, in any case, does not eliminate the problem of wart recurrence;
- cryotherapy: it consists in freezing the affected area with liquid nitrogen;
- keratolytic preparations: they accelerate the wart maturation cycle, making it rise to the surface and allowing spontaneous detachment;
- intralesional injections: injections of interferon into the wart itself, in order to induce apoptosis of virus-infected cells;
- laser therapy: it consists of burning the wart by laser;
- vitamin E application: locally applied vitamin E, in oil preparations also used as a skin anti-irritation lotion, leads to the elimination of the wart, probably improving the healing capacity.

These treatments are mostly invasive and have a probability of success of no more than 70%.

There is therefore a need for a treatment of HPV cutaneous infections, in particular benign cutaneous infections such as warts and related manifestations, which is effective and minimally invasive.

Recently, the use of acetylsalicylic acid for the treatment of warts and papillomas has been proposed by the same inventor of the present patent application. The international application no. PCT/IB2016/055300 describes pharmaceutical compositions, in particular patches or plasters, containing ASA in solid form or incorporated in hydrophilic and hydrophobic gels or in cyclodextrins.

Acetylsalicylic acid (ASA) belongs to the class of non-steroidal anti-inflammatory drugs (NSAIDs). ASA is a salicylic acid derivative, distinguished by the presence of an acetyl group in position 2, responsible for the anti-inflammatory activity of the molecule. ASA exerts an inflammatory action by inhibiting the synthesis of prostaglandins by serine acetylation at the active site of the cyclooxygenase enzyme (COX). At low doses (75-81 mg/day) the action of ASA is selective at platelet level, where it irreversibly inhibits the serine 530 of COX1, exerting an antithrombotic effect. At higher doses (650-4000 mg/day), ASA inhibits COX1 and COX2, blocking prostaglandin synthesis and providing an antipyretic and analgesic effect. Other mechanisms of action of the molecule have been studied or proposed to explain the many pharmacological properties thereof, but little is known about a possible antiviral activity of ASA.

Although the formulations described in the international application no. PCT/IB2016/055300, in particular plasters or patches, have proved to be effective in the treatment of warts, papillomas and warts, they do not solve all the problems related to this type of application. In particular, a patch has the disadvantage of being unaesthetic, troubling and easily detachable when the part on which it is applied is in contact with water.

Moreover, the ASA contained in said patches showed a non-optimal stability, giving rise, after some months of storage at room temperature, to a non-negligible percentage of salicylic acid as a product of the hydrolysis of ASA.

There are various technical problems that an ideal formulation should solve. In particular, the formulations should:

- Contain effective but non-toxic concentrations of the active ingredient, i.e. the minimum concentration sufficient to effectively remove the lesion without damaging the deeper cutaneous layers;
- Contain active ingredient concentrations such as not to enter the bloodstream and not to exert systemic effects, in particular, ASA should be included in concentrations having only local effects, without the risk to entry the bloodstream with consequent undesirable systemic effects;
- Be preferably water resistant, so that they are not detached or washed away during daily hygiene operations, or they can be applied even when the subject frequents pools, beaches, etc. In the latter case, in fact, the formulation would help to protect the lesion against further contamination by pathogens and to limit the contagion of other subjects as it would block the release of micro-infected skin into the environment;
- Maximize the stability of ASA against hydrolysis;
- Remove the lesion quickly, increasing the subject's compliance;
- Allow the subject to self-apply, at home, without turning to the doctor;
- Be easy to use, understood as ease of application on the lesion, also for use in subjects such as children, and only on the lesion, without being distributed on surrounding healthy tissues;
- Be comfortable and discreet once applied, without creating discomfort to the subject;
- Resist friction and rubbing, so that the medication does not go away doing daily activities, such as rubbing against clothes, fabrics, linens, footwear and everyday objects, in view of the fact that very often these lesions affect the skin of hands, feet and genital organs;
- Have a low cost.

SUMMARY OF THE INVENTION

Therefore, the present invention relates to a collodion-based composition comprising acetylsalicylic acid, as outlined in the attached claims 1 to 3.

The invention also relates to a composition comprising acetylsalicylic acid and glycols, as outlined in the attached claims 4 to 10.

The invention further relates to collodion and glycols-based compositions, comprising acetylsalicylic acid as the unique active ingredient or optionally containing in addition a substance with antivascular activity and/or a substance helping the treatment of eliminating growths or warts and/or a substance with analgesic or anesthetic action, as outlined in the attached claims 11 to 16.

The invention further relates to the compositions of the invention for use in the treatment of HPV cutaneous infections, in particular benign infections such as warts, papillomas and condylomas, as outlined in the attached claims 17 to 18.

The invention still further relates to a kit comprising a composition comprising acetyl salicylic acid and a device for the mechanical removal of the lesion.

The text of the appended claims forms an integral part of the present specification.

Further features and advantages of the process according to the invention will become apparent from the following description of preferred embodiments, given by way of non-limiting example.

DETAILED DESCRIPTION OF THE INVENTION

Figure 1:
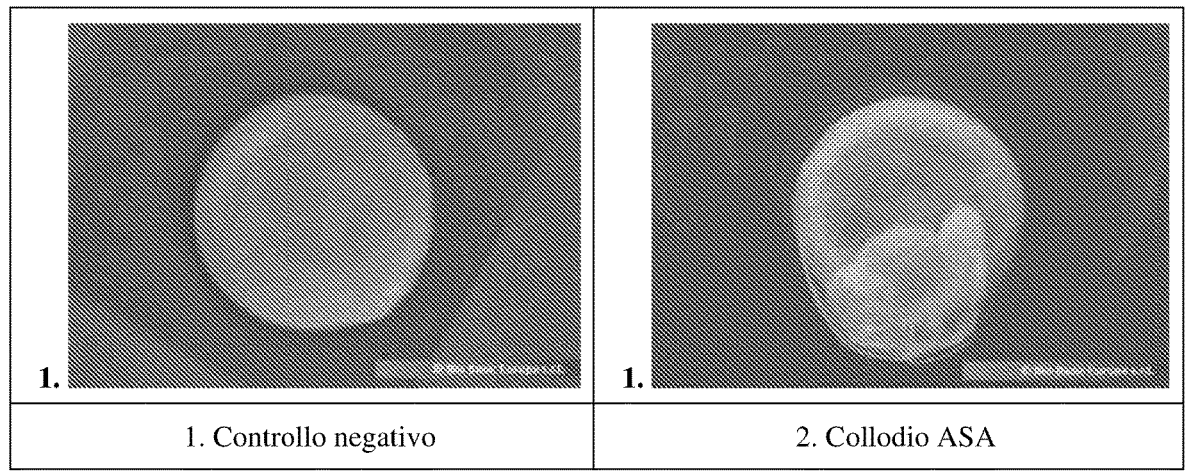
FIG. 1 shows stereo microscope photographs of a fabric treated with a collodion-based composition of the invention versus a control fabric.

According to a first embodiment, the present invention relates to a collodion-based composition comprising acetylsalicylic acid for use in the treatment of HPV cutaneous infections, in particular of benign cutaneous infections such as warts, both common and plantar or flat, papillomas, condylomas and the like.

The collodion is a solution of pyroxilin in ether/alcohol. The pyroxilin (gun-cotton, fulminant cotton or collodion cotton) is a mixture of cellulose nitro-ethers with a predominance of dinitro-cellulose.

The collodion is no longer registered in the Italian Official Pharmacopoeia (FUI), but, according to the VI edition thereof, it is prepared by dissolving 1 part of pyroxilin in 4 parts of alcohol at 96° and 12 parts of ethyl ether. Once applied to the skin, the solvent evaporates rapidly leaving an occlusive film that can protect small lesions, block a surgical bandage or keep drugs, previously dissolved in it, in long-lasting contact with the epidermis.

By adding virgin castor oil to the collodion, elastic collodion is obtained, more resistant and adaptable to skin folds. The FUI VI ed. do not include other substances, while the US Pharmacopoeia also inserts camphor and the British Pharmacopoeia colophony (Flexible Collodion USP and BP).

The elastic collodion can be prepared starting from the indications available in the Austrian Pharmacopoeia or in the German NRF formulary:

Collodion 97 parts by weight
Castor oil 3 parts by weight.

The collodion can be used at 5% by weight of pyroxilin in an alcohol/ethyl ether mixture.

In preferred embodiments, the composition of the invention comprises from 10% to 30% by weight of acetylsalicylic acid and from 50% to 80% by weight, more preferably from 50% to 70% by weight, of collodion or elastic collodion, obtained as described above, the remaining part being solvent. The elastic collodion is particularly preferred. Preferably, the solvent is ethyl alcohol or a mixture of ethyl alcohol and ethyl ether, more preferably an ethyl alcohol/ethyl ether mixture about 1:1 by weight.

In preferred embodiments, the composition of the invention comprises from 10% to 25% by weight of acetylsalicylic acid, from 50% to 70% by weight of collodion or elastic collodion, obtained as described above, and from 5% to 15% by weight of a glycol, the remaining part being solvent. The glycol is preferably propylene glycol (1,2-propanediol). The solvent is preferably a 1:1 mixture of ethanol/ethyl ether. The collodion is preferably elastic collodion.

A particularly preferred composition has the following percentage composition by weight:

| | |
|---|---|
| ASA | 15-22% |
| Ethyl ether | 7-11% |
| Pure ethyl alcohol | 7-11% |
| Elastic collodion | 50-57% |
| Propylene glycol | 7-13%. |

The collodion- or collodion and glycol-based compositions can be prepared according to the following example.

Pure ethyl alcohol (9 g) was placed in a closed vessel and the granulated ASA (18 g) was poured into it, stirring continuously, until the powder was pre-dispersed. Collodion or elastic collodion (54 g) was added with ethyl ether (9 g) and mixing was continued until complete solubilization. Then the glycol (propylene glycol, 10 g) was added. In order to facilitate solubilization, a water bath at a temperature of 35-40° C. was used. In the collodion alone-based preparations, glycol is omitted. In both cases, a different solvent can be used.

The above described ASA and collodion- or ASA, collodion and glycol-based compositions are in the form of a solution and they can be administered on the treatment site (wart, papilloma, condyloma or similar) by a dropper or a pipette. Considering that the extension of a wart or of a condyloma is generally between 1 mm and 10 mm, an amount of about 10 microliters of this solution is normally sufficient to cover the intervention area so as to form a film thereon.

In certain embodiments of the invention, the composition comprising acetylsalicylic acid further comprises a glycol.

The glycol is preferably selected from propylene glycol (1,2-propanediol), 1,3-propanediol, butylene glycol, pentylene glycol or mixtures thereof.

In preferred embodiments, the composition contains ASA between 5 and 30% by weight and glycol between 1% and 30% by weight.

The composition will also contain further excipients depending on the type of formulation to be prepared. In the following formulations, "PVP" means "polyvinylpyrrolidone" and "VP/VA copolymer" means "polyvinylpyrrolidone/vinyl acetate copolymer."

In certain embodiments, the composition of ASA and glycols is a liquid solution to be applied, e.g., by brushing, a spray or a gel. Preferably, this composition comprises (composition by weight):

| | |
|---|---|
| ASA | 5-30% |
| Glycol | 1-30% |
| Cellulose polymer | 0-30% |
| Acrylic polymer | 0-35% |
| Solvent | q.s. |

Particularly preferred forms of compositions in the form of a brushable solution are the following:

Formulation a (Brushable Solution)

| | |
|---|---|
| ASA | 5-30% |
| 1,2-propanediol, 1,3-propanediol o butylene glycol or pentylene glycol | 1-10% |
| Hydroxypropyl cellulose or hydroxypropyl methylcellulose or hydroxyethyl cellulose | 1-10% |
| VP/VA copolymer | 1-15% |
| PVP | 1-5% |
| Water | 0-5% |
| Ethyl alcohol | qs to 100 |

This formulation is obtained by mixing a part of alcohol and the polymers until completely dissolved in a suitable system provided with a homogenization turbine. In the remaining part or alternatively in the propylene glycol, ASA is then dissolved, mixing until complete dissolution and joining the whole to the previous solution. Finally, the remaining water is added.

Formulation B (Brushable Solution)

| | |
|---|---|
| ASA | 5-30% |
| 1,2-propanediol, 1,3-propanediol or butylene glycol or pentylene glycol | 1-10% |
| Nitrocellulose | 1-30% |
| Hydroxypropyl cellulose | 1-10% |
| Castor oil | 1-5% |
| Ethyl acetate | 1-30% |
| Ethyl alcohol | qs to 100 |

Formulation C (Brushable Solution)

| | |
|---|---|
| ASA | 5-30% |
| 1,2-propanediol, 1,3-propanediol or butylene glycol or pentylene glycol | 1-10% |
| Hydroxyethyl cellulose | 1-10% |
| VP/VA copolymer | 1-15% |
| Polyvinyl alcohol | 1-5% |
| Ethyl alcohol | qs to 100 |

Formulation D (Brushable Solution)

| | |
|---|---|
| ASA | 5-30% |
| 1,2-propanediol, 1,3-propanediol or butylene glycol or pentylene glycol | 1-10% |
| Acrylic ester polymer | 5-35% |
| Isooctane | 10-90% |

Particularly preferred forms of compositions in the spray form are the following:

Formulation E (Spray)

| | |
|---|---|
| ASA | 5-30% |
| 1,2-propanediol, 1,3-propanediol or butylene glycol or pentylene glycol | 1-10% |
| Acrylic ester polymer | 1-20% |
| Polyurethane | 1-20% |
| Ethyl ether | 1-20% |
| Ethyl alcohol | 10-80% |
| Water | qs to 100 |

Formulation F (Spray Aerosol)

| ASA | 5-30% |
|---|---|
| 1,2-propanediol, 1,3-propanediol or butylene glycol or pentylene glycol | 1-10% |
| Hydroxypropyl cellulose or hydroxypropyl methylcellulose or hydroxyethylcellulose | 1-10% |
| VP/VA copolymer | 1-15% |
| PVP | 1-5% |
| Ethyl alcohol | 10-40% |
| Water | 0-5% |
| Butane, propane or isobutane | qs to 100 |

Formulation G (Gel)

| ASA | 5-30% |
|---|---|
| 1,2-propanediol, 1,3-propanediol or butylene glycol or pentylene glycol | 1-10% |
| Hydroxypropyl cellulose or hydroxypropyl methylcellulose or hydroxyethylcellulose | 1-10% |
| Acrylic ester polymer | 1-5% |
| VP/VA copolymer | 1-15% |
| Ethyl alcohol | 10-40% |
| Water | qs to 100 |

The gel is prepared by hydrating the acrylic ester polymer in water and then stirring the solution until the gel is obtained. The polymers are solubilized in ethyl alcohol until complete dissolution in a suitable system provided with a homogenizing turbine. ASA is then dissolved in another aliquot of ethyl alcohol or glycol and the whole is mixed until complete dissolution, and then added to the previously prepared solution.

Formulation H (Vaginal Gel)

| ASA | 5-30% |
|---|---|
| 1,2-propanediol, 1,3-propanediol or butylene glycol or pentylene glycol | 1-30% |
| Hydroxypropyl cellulose or hydroxypropyl methylcellulose or hydroxyethylcellulose | 1-10% |
| Polycarbophil | 0-1% |
| Parabens mixture | 0-1% |
| Water | qs to 100. |

According to a different aspect of the invention, the following compositions by weight are provided.

Formulation I (Ointment)

| Cetyl alcohol | 1-5% |
|---|---|
| Lanolin alcohol or lanolin ester | 0-15% |
| Petrolatum | 1-60% |
| Paraffinum liquidum | 1-20% |
| Water | qs to 100 |
| Acetylsalicylic acid | 5-30% |

Formulation L (Vaginal Ovules)

| Semi-synthetic glycerides | qs |
|---|---|
| Polycarbophil | 0-1% |
| Acetylsalicylic acid | 5-30%. |

All the described above compositions can be prepared according to conventional methods, such as those described in *Remington, The Science and Practice of Pharmacy*, Edited by Allen, Loyd V., Jr, 22nd edition, 2012.

In preferred embodiments, the dosage of ASA is from 0.3 to 1.2 g/day, preferably from 0.5 to 1 g/day.

In certain embodiments, the collodion-based compositions of the invention, with or without a glycol, or those comprising ASA in association with a glycol, may contain a substance with antivascular activity and/or a substance helping the treatment of eliminating growths or warts and/or a substance with analgesic or anesthetic action. The amount of such substances in the composition of the invention will depend on the nature of the substance and on the effect to be imparted and will generally be in the range between 0.01% and 10% by weight.

Examples of preferred substances that can be used in the composition of the invention are the following:

Substances with Antivascular Action
Dehydro-α-lapachone
Combretastatine
Extracts of *Piptadiniastrum africanum*
Extracts of *Kigelia africana*
Extracts of *Centella asiatica*
Extracts of *Chaemocrista nigricans*
Oleuropein/olive leaf extracts.

Substances with Properties Helping the Treatment of Growths and Warts

Extracts of *Agoseris glauca, Apocynum cannabinum, Argemone mexicana, Asclepias eriocarpa, Asclepias hallii, Asclepias lanceolata, Asclepias purpurascens, Asclepias quadrifolia, Asclepias rubra, Asclepias speciosa, Asclepias syriaca, Calendula arvensis, Calendula officinalis, Caltha leptosepala, Caltha natans, Caltha palustris, Chelidonium majus, Cichorium intybus, Coix lacryma-jobi, Delphinium staphisagria, Diospyros virginiana, Dipsacus fullonum, Dipsacus sativus, Drosera rotundifolia, Euphorbia hirta, Euphorbia lathyris, Euphorbia serpyllifolia, Ficus carica, Ficus palmata, Impatiens aurella, Impatiens balsamina, Impatiens capensis, Impatiens ecalcarata, Impatiens occidentalis, Impatiens parviflora, Juniperus sabina, Lactuca canadensis, Mercurialis annua, Mercurialis perennis, Monotropa uniflora, Ocimum minimum, Opuntia compressa, Paulownia tomentosa, Podophyllum peltatum, Ranunculus acris, Rhus diversiloba, Rhus typhina, Salvia lyrata, Sempervivum tectorum, Sonchus oleraceus, Symphoricarpos albus laevigatus, Taraxacum officinale, Zea mays.*

Substances with Analgesic/Anesthetic Action

Extracts of *Aconitum carmichaelii, Aconitum ferox, Aconitum fischeri, Aconitum kusnezoffii, Aconitum lycoctonum, Aconitum uncinatum, Aconitum volubile, Arisaema thunbergii, Asarum heterotropoides, Asarum sieboldii, Capsicum frutescens, Coptis chinensis, Coptis teeta, Datura metel, Fritillaria sewerzowii, Gleditsia macracantha, Gleditsia triacanthos, Mentha arvensis, Mentha arvensis piperascens, Monarda menthifolia, Rhododendron molle, Salix pulchra, Tagetes lucida, Zanthoxylum bungeanum, Zanthoxylum schinifolium.*

EXPERIMENTAL

Evaluation of the Keratolytic Effects of the Compositions of the Invention on Pigskin by Analysis of Cutaneous Roughness The pigskin is histologically similar to the human skin [Gray and Yardley, 1975; Wester et al., 1998]. Even the average density of hair follicles is similar: 20/cm2 for pig ear skin compared to 14-32/cm2 for human forehead skin [Jacobi et al., 2007]. Therefore, the pigskin is a convenient substrate for performing keratolytic efficacy studies.

For the execution of the assays described herein, the pigskin was obtained from a local slaughterhouse (San Giuliano Terme, Pisa, Italy). The skin was washed with water and the visible bristles were cut at the base.

The composition elastic collodion with 20% ASA-based described above was subjected to this assay, in addition to a negative control consisting of pigskin without any treatment.

The composition was applied on the pigskin in such a way as to cover a circular surface of 6 mm, in triplicate, and was kept in contact with the pigskin for 14 hours. After this time, a cutaneous roughness measurement was performed by the use of an Intelligent Skin Analysis System (GBS-1800) digital dermatoscope by Maikong Industry. Each evaluation was carried out in such a way as to have a CV (coefficient of variation on the measure) of less than 15%.

The results are given in the table below as mean+/−SD. The effects of the various treatments versus the controls were evaluated by t-test.

|  | Cutaneous roughness mean value | SD | n | p* vs control |
|---|---|---|---|---|
| Negative control | 2.6 | 0.07 | 2 | — |
| Elastic collodion with 20% ASA | 2.19 | 0.165 | 4 | 0.03 |

*p < 0.05 indicates a statistically significant difference.

Evaluation of the Keratolytic Effects of the Compositions of the Invention on Reconstructed Human Tissues The tissues were treated with the samples for 14 hours. At the end of this period they were removed from the support, washed in PBS and then fixed in a 4% paraformaldehyde solution.

The fixed tissues were first subjected to macroscopic analysis to highlight the presence of any visible lesions in the keratinocytes superficial layer and then subjected to histochemical analysis. For this purpose, the tissues were first dehydrated in the ascending scale of alcohols (70°-85°-90°-100°) for 60-100 minutes at each step, diaphanized with xylene and transferred to melted in oven-paraffin at 51° C. for 2 hours, then at 60° C. for 1 hour and allowed to solidify at room temperature.

For staining with hematoxylin/eosin, the sections laid on slides were made paraffine-free in xylene for 15 minutes and rehydrated following the descending scale of alcohols to water. The slides were then immersed in Emallume by Mayer (Hematoxylin) for 3 minutes, washed in running water and then immersed in a 1% Eosin G solution for 3 minutes. At the end of the staining, the sections were dehydrated following the ascending scale of the alcohols and mounted with DPX.

Based on the macroscopic evaluation (photographs taken from the stereomicroscope), as shown in FIG. 1, in the treated tissues an alteration of the most superficial layer is observed. The damage is particularly evident in the tissues treated with collodion-based composition.

Figure 2:
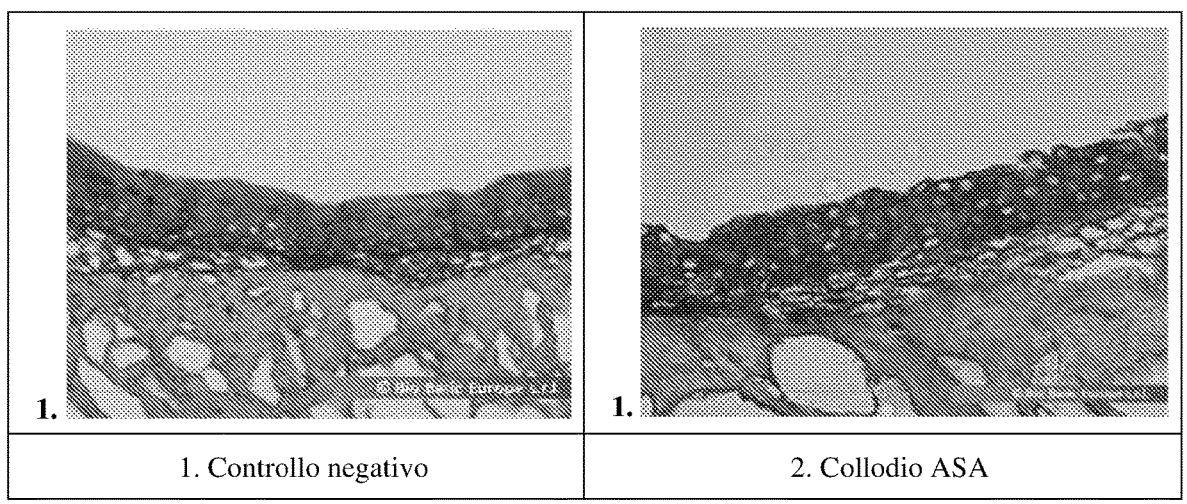
FIG. 2 shows photographs for the histochemical evaluation of a fabric treated with a collodion-based composition of the invention versus a control fabric.

Based on the histochemical evaluation (FIG. 2), in the collodion-treated tissues the absence of the superficial corneous layer is observed, which is still present in the control tissues.

Experiments Comparing Different ASA-Containing Compositions on the Ultrastructure of Artificial Constructs of Human Skin (SkinEthic)

The following compositions were evaluated in comparison.

Composition 1—Solution with Elastic Collodion

The composition, prepared as previously described, contained (percentages by weight):

| ASA | 20% |
|---|---|
| Ethyl ether | 10% |
| Pure ethyl alcohol | 10% |
| Elastic collodion | 60%. |

Composition 2—Solution with Elastic Collodion+Propylene Glycol

The composition, prepared as previously described, contained (percentages by weight):

| ASA | 18% |
|---|---|
| Ethyl ether | 9% |
| Pure ethyl alcohol | 9% |
| Elastic collodion | 54% |
| Propylene glycol | 10%. |

Composition 3—Solution with Con Propylene Glycol

The composition 3 contained exclusively propylene glycol, at a purity of more than 99%.

Composition 4—Hydrophilic Gel

The composition contained (percentages by weight):

| ASA | 2% |
|---|---|
| Pure ethyl alcohol | 18% |
| Vegetable glycerin | 5% |
| Propylene glycol | 5% |
| Xanthan gum | 2.5% |
| Carrageenan | 1.5% |
| Phenoxyethanol | 0.5% |
| Purified water | q. s. to 100 |

Preparation:

Solubilize ASA in ethanol up to a perfectly clear solution, then incorporate it slowly and in portions inside the gel.

For the gel: pre-disperse the xanthan gum and the carrageenan in the glycerin+propylene glycol, then add the water, bring the mixture to 55-60° C. and homogenize with the blades and turbine, under vacuum.

Cool the gel to room temperature and add the phenoxyethanol, then add the alcohol ASA solution.

Composition 5—Petrolatum-Based ASA Ointment

The composition contained (percentages by weight):

| ASA | 20% |
|---|---|
| Petroleum jelly/petrolatum | 78% |
| Liquid paraffin | 2%. |

Preparation:

Mix together the ASA in portions in the petroleum jelly until homogeneity; then add the liquid paraffin. To further refine the preparation, micronized ASA and an ointment refiner were used to obtain a product without crystals that could be perceived by touch and increase the contact surface of the active ingredient and therefore the effectiveness thereof.

Composition 6—Hydrophilic Emulsion

The composition contained (percentages by weight):

| ASA | 2% |
|---|---|
| Pure ethyl alcohol | 18% |
| Amphiphilic base | 80%. |

Preparation:

Solubilize the ASA in ethanol up to a perfectly clear solution, then incorporate it slowly and in portions inside the amphiphilic base, with accurate and continuous stirring by means of blades. Operate under vacuum in a conventional machine.

Base composition: water q.s. at 100%; petrolatum 25.5%; propylene glycol 10%; caprylic/capric triglyceride 7.5%; PEG-8 stearate 7%; cetearyl alcohol 6%; glyceryl stearate 4%; phenoxyethanol 0.5%; sodium benzoate 0.4%; potassium sorbate 0.3%; citric acid to pH.

Composition 7—Patch

The composition contained (percentages by weight):

| | |
|---|---|
| ASA | 5%. |

Preparation:

The individual raw materials were weighed: a conventional polymeric adhesive in the preparation of patches was used for the preparation of a bulk adhesive, to which the ASA was added.

The bulk adhesive thus obtained was spread on a polyester support. The smear was dried inside drying ovens; then, the semi-finished product coming out from the ovens was coupled with a polyurethane film and subsequently wrapped in a "mother" coil.

The "mother" coil has been cut into other smaller coils. The cut coils were subjected to automatic die cutting in order to obtain liners of 10 round patches with a diameter of 12 mm. The obtained round patches were packaged.

The amounts of ASA used in the various compositions were determined starting from various tests and selecting among those giving rise to a macroscopically stable composition, i.e. wherein the ASA did not separate as solid from the composition.

Artificial Constructs of Human Skin

SkinEthic™ RHE/S/17 reconstituted human epidermis samples were used. This is an in vitro reconstituted human epidermis from normal human keratinocytes grown on a polycarbonate filter at the air-liquid interface.

The tissue samples were removed from the protective agarose and incubated in a multiwell with 6 wells with 1 ml of maintenance medium per well. After approximately hours of incubation, the samples were treated as follows:

- 100 μl of solution of the compositions 1, 2, 3 and pure water (control) were affixed above respective epidermal sheets using a micropipette;
- An abundant amount of mixture of the compositions (hydrophilic gel), 5 (ointment) and 6 (hydrophilic emulsion) was spread over respective epidermal sheets using cotton buds;
- A small piece of patch (composition 7) was glued onto an epidermal sheet.

After about 14 hours of incubation with the described-above compositions, the epidermis inserts were cut and fixed in 500 microliters of fixative (glutaraldehyde 2.5%, paraformaldehyde 2% in cacodylate buffer 0.1 M at pH 7.4) for 2 hours at room temperature.

After trimming small rectangles of fabric, the samples were included in an epoxy resin. Ultra-thin slices were obtained and placed on copper screens, then stained with uranyl acetate and lead citrate.

Figure 3:
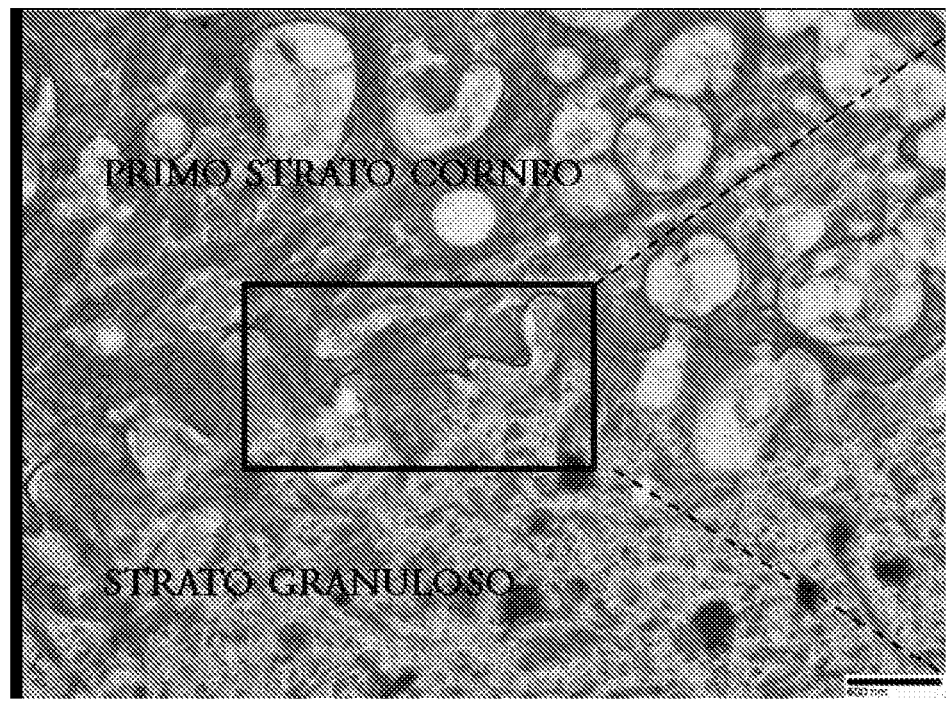
FIG. 3 shows a photograph for the histochemical evaluation of the granulose layer, of the first corneum layer and of the interposed desmosomes, on artificial constructs of untreated human skin.

The TEM electron microscopic observation of the untreated epidermal tissue (control sample treated with water alone) showed a granular layer joint by numerous desmosomes to the first of 24-25 corneocyte layers (FIG. 3).

Figure 4:
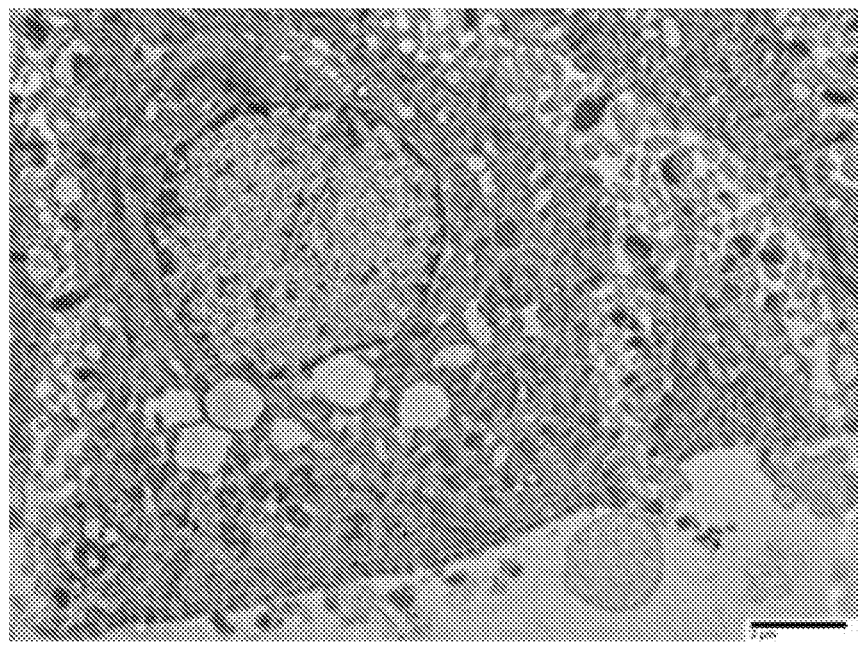
FIG. 4 shows a photograph (2000×) for the histochemical evaluation of the basal layer on artificial constructs of untreated human skin.
Figure 5:
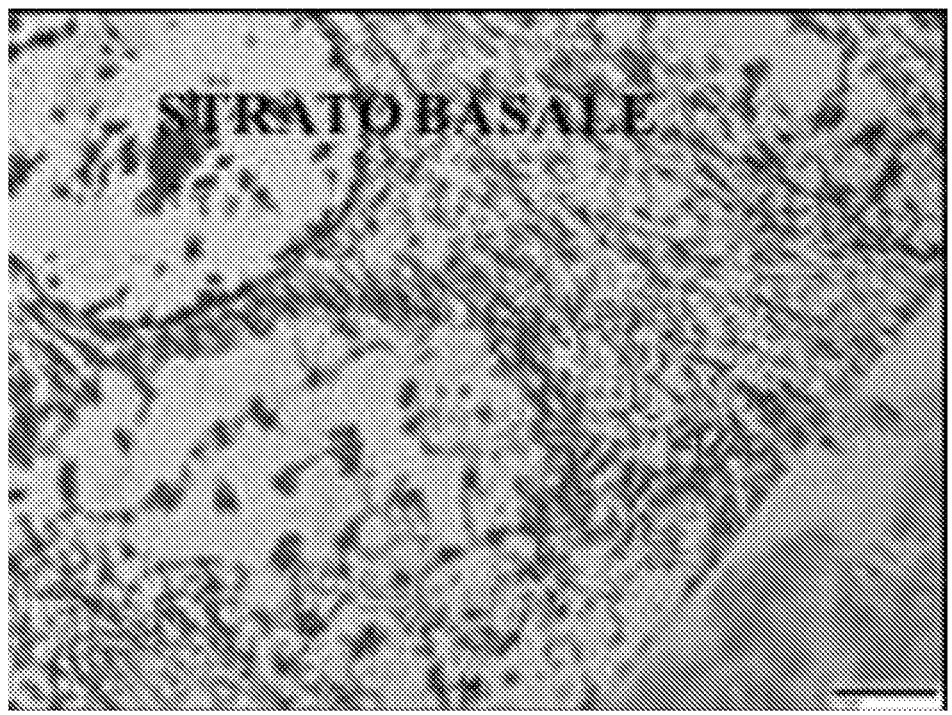
FIG. 5 shows a photograph for the histochemical evaluation of the basal layer on artificial constructs of human skin treated with the compositions ASA- and collodion-based of the present invention.

Following treatment, the overall appearance of the basal, spinous and granular layers was preserved and similar to the control in the samples treated with the compositions 3, 7 and 5 (FIG. 4). In the samples treated with the compositions 1, 2 and 4 all the cellular layers have a necrotic appearance (FIG. 5), index of very high cytotoxicity. In the samples treated with the composition 6 a general cellular suffering in the spinous layer is present with some necrotic cells and some pyknotic nuclei suggesting the induction of apoptotic processes.

The number of corneocyte layers remaining on the sample after the treatment has therefore been determined, an important parameter to evaluate the effectiveness of the treatment, as it is an indicator of the residual thickness of the corneum layer.

Table 1 below shows the results of this determination.

TABLE 1

Number of corneocyte layers left after treatment with the compositions 1 to 7

| Composition | N. of corneocyte layers |
|---|---|
| 1 | 10-12 |
| 2 | 1-4 |
| 3 | 19-20 |
| 4 | 14-15 |
| 5 | 25 |
| 6 | 25 |
| 7 | 14-15 |
| Control (not-treated) | >25 |

The data set out in the table show a substantial ineffectiveness of the compositions 5 (ointment) and 6 (hydrophilic emulsion); a poor efficacy of the composition 3 (propylene glycol-based composition); a medium efficacy of the compositions 4 (hydrophilic gel) and 7 (patch); a more marked efficacy of the composition (collodion-based composition); an extremely high efficacy of the composition 2 (collodion+propylene glycol-based composition).

The latter data thus shows a noticeable synergistic effect of the combination of ASA, collodion and propylene glycol, since the result of the composition 2 cannot be considered an additive effect of those reported for compositions 1 and 3.

It can also be noted that the amount of ASA in the composition is not a discriminant between active or inactive composition, since, for example, the compositions 4 (ASA 2%) and 7 (ASA 5%) are more active than the composition 5 (ASA 20%).

Stability of the Compositions

The amount of salicylic acid (SA) present in some compositions of the invention after storage at room temperature for a period of about 5 months was determined. This evaluation was carried out using the HPLC/UV method validated according to the EUEP and USP Pharmacopoeias. The results are as follows:

| | |
|---|---|
| composition 7 (patch) | SA 75.86% by weight |
| composition 1 (collodion) | SA 15.57% by weight |
| composition 2 (collodion + prop. glycol) | SA about 7% by weight. |

Specific Examples of Compositions

Formulation A (Brushable Solution)

| | |
|---|---|
| ASA | 10% |
| 1,2-propanediol, 1,3-propanediol or butylene glycol or pentylene glycol | 10% |
| Hydroxypropyl cellulose or hydroxypropyl methylcellulose or hydroxyethyl cellulose | 10% |
| VP/VA copolymer | 10% |
| PVP | 3% |
| Water | 3% |
| Ethyl alcohol | 54% |

Formulation B (Brushable Solution)

| | |
|---|---|
| ASA | 20% |
| 1,2-propanediol, 1,3-propanediol or butylene glycol or pentylene glycol | 10% |
| Nitrocellulose | 20% |
| Hydroxypropyl cellulose | 10% |
| Castor oil | 4% |
| Ethyl acetate | 26% |
| Ethyl alcohol | 10% |

Formulation C (Brushable Solution)

| | |
|---|---|
| ASA | 15% |
| 1,2-propanediol, 1,3-propanediol or butylene glycol or pentylene glycol | 8% |
| Hydroxyethyl cellulose | 10% |
| VP/VA copolymer | 12% |
| Polyvinyl alcohol | 5% |
| Ethyl alcohol | 50% |

Formulation D (Brushable Solution)

| | |
|---|---|
| ASA | 25% |
| 1,2-propanediol, 1,3-propanediol or butylene glycol or pentylene glycol | 5% |
| Acrylic ester polymer | 25% |
| Isooctane | 45% |

Formulation E (Spray)

| | |
|---|---|
| ASA | 10% |
| 1,2-propanediol, 1,3-propanediol or butylene glycol or pentylene glycol | 10% |
| Acrylic ester polymer | 18% |
| Polyurethane | 12% |
| Ethyl ether | 20% |
| Ethyl alcohol | 20% |
| Water | 10% |

Formulation F (Aerosol Spray)

| | |
|---|---|
| ASA | 25% |
| 1,2-propanediol, 1,3-propanediol or butylene glycol or pentylene glycol | 10% |
| Hydroxypropyl cellulose or hydroxypropyl methylcellulose or hydroxyethyl cellulose | 5% |
| VP/VA copolymer | 15% |
| PVP | 4% |
| Ethyl alcohol | 20% |
| Water | 5% |
| Butane, propane or isobutane | 16% |

Formulation G (Gel)

| | |
|---|---|
| ASA | 15% |
| 1,2-propanediol, 1,3-propanediol or butylene glycol or pentylene glycol | 7% |
| Hydroxypropyl cellulose or hydroxypropyl methylcellulose or hydroxyethyl cellulose | 8% |
| Acrylic ester polymer | 5% |
| VP/VA copolymer | 10% |
| Ethyl alcohol | 30% |
| Water | 25% |

Formulation H (Vaginal Gel)

| | |
|---|---|
| ASA | 20% |
| 1,2-propanediol, 1,3-propanediol or butylene glycol or pentylene glycol | 20% |
| Hydroxypropyl cellulose or hydroxypropyl methylcellulose or hydroxyethyl cellulose | 10% |
| Polycarbophil | 1% |
| Parabens mixture | 1% |
| Water | 48% |

Formulation I (Solution)

| | |
|---|---|
| ASA | 20% |
| Ethyl ether | 10% |
| Pure ethyl alcohol | 10% |
| Elastic collodion | 60%. |

Formulation L (Solution)

| | |
|---|---|
| ASA | 18% |
| Ethyl ether | 9% |
| Pure ethyl alcohol | 9% |
| Elastic collodion | 54% |
| Propylene glycol | 10%. |

The invention further relates to a kit comprising an amount of the composition of the invention for a single or multiple application and a device for the mechanical removal of the lesion.

Useful devices can be, for example, a file to be used several times, a series of disposable files, pumice stones or the like, with abrasive mechanical properties. The abrasive material must have a granulometry such as to remove only the tissue affected by the lesion, avoiding bleeding. A series of disposable files should be preferred, to avoid that the micro-scales of infected skin removed from the file can remain in the environment and cause any contagion.

It is evident that only some particular embodiments of the present invention have been described, to which the technical expert will be able to make all the modifications necessary for the adaptation thereof to particular applications, without departing from the scope of protection of the present invention.

The invention claimed is:

1. A collodion-based composition comprising:
   10% to 25% by weight acetylsalicylic acid (ASA);
   50% to 70% by weight collodion or elastic collodion;
   5% to 15% by weight a glycol; and,
   solvent.

2. A composition according to claim 1, wherein said collodion is elastic collodion comprising a mixture of collodion and castor oil.

3. A composition according to claim 1, wherein the glycol is selected from 1,3-propanediol, 1,2-propanediol, butylene glycol and pentylene glycol or mixtures thereof.

4. A composition according to claim 1, wherein said composition is a brushable liquid solution, a spray composition or a gel, and further comprising:

| | |
|---|---|
| Cellulose polymer | 0-30% by weight |
| Acrylic polymer | 0-35% by weight |
| Solvent | q.s. to 100. |

5. A composition according to claim 4, wherein said composition is a brushable liquid solution having one of the following compositions by weight:

Formulation A comprising:

| | |
|---|---|
| Hydroxypropyl cellulose or hydroxypropyl methylcellulose or hydroxyethyl cellulose | 1-10% |
| polyvinylpyrrolidone/Vinyl Acetate (VP/VA) copolymer | 1-15% |
| polyvinylpyrrolidone (PVP) | 1-5% |
| Water | 0-5% |
| Ethyl alcohol | qs to 100 |

Formulation B comprising:

| | |
|---|---|
| Nitrocellulose | 1-30% |
| Hydroxypropyl cellulose | 1-10% |
| Castor oil | 1-5% |
| Ethyl acetate | 1-30% |
| Ethyl alcohol | qs to 100 |

Formulation C comprising:

| | |
|---|---|
| Hydroxyethyl cellulose | 1-10% |
| polyvinylpyrrolidone/Vinyl Acetate (VP/VA) copolymer | 1-15% |
| Polyvinyl alcohol | 1-5% |
| Ethyl alcohol | qs to 100 |

Formulation D comprising:

| | |
|---|---|
| Acrylic ester polymer | 5-35% |
| Isooctane | 10-90%. |

6. A composition according to claim 4, wherein said composition is a spray having one of the following compositions by weight:

Formulation E comprising:

| | |
|---|---|
| Acrylic ester polymer | 1-20% |
| Polyurethane | 1-20% |
| Ethyl ether | 1-20% |
| Ethyl alcohol | 10-80% |
| Water | qs to 100 |

Formulation F comprising:

| | |
|---|---|
| Hydroxypropyl cellulose or hydroxypropyl methylcellulose or hydroxyethylcellulose | 1-10% |
| VP/VA copolymer | 1-15% |
| PVP | 1-5% |
| Ethyl alcohol | 10-40% |
| Water | 0-5% |
| Butane, propane or isobutane | qs to 100. |

7. A composition according to claim 4, wherein said composition is a gel having one of the following compositions by weight:

Formulation G comprising:

| | |
|---|---|
| Hydroxypropyl cellulose or hydroxypropyl methylcellulose or hydroxyethylcellulose | 1-10% |
| Acrylic ester polymer | 1-5% |
| VP/VA copolymer | 1-15% |
| Ethyl alcohol | 10-40% |
| Water | qs to 100 |

Formulation H comprising:

| | |
|---|---|
| Hydroxypropyl cellulose or hydroxypropyl methylcellulose or hydroxyethylcellulose | 1-10% |
| Polycarbophil | 0-1% |
| Parabens mixture | 0-1% |
| Water | qs to 100. |

8. A composition according to claim 1, wherein: the glycol is propylene glycol, and/or the solvent is a 1:1 mixture of ethanol/ethyl ether, and/or collodion is elastic collodion.

9. A composition according to claim 1, having the following percentage composition by weight:

| | |
|---|---|
| ASA | 15-22% |
| Ethyl ether | 7-11% |
| Pure ethyl alcohol | 7-11% |
| Elastic collodion | 50-57% |
| Propylene glycol | 7-13%. |

10. A composition according to claim 1, further comprising a substance with antivascular activity and/or a substance helping the treatment of eliminating growths or warts and/or a substance with analgesic or anesthetic action.

11. A composition according to claim 10, wherein:
said substance with antivascular activity is selected from Dehydro-α-lapachone, Combretastatine, Extracts of *Piptadiniastrum africanum*, Extracts of *Kigelia africana*, Extracts of *Centella asiatica*, Extracts of *Chaemocrista nigricans*, Oleuropein/olive leaves extracts or mixtures thereof;
said substance helping the treatment of eliminating growths or warts is selected from extracts of *Agoseris glauca, Apocynum cannabinum, Argemone mexicana, Asclepias eriocarpa, Asclepias hallii, Asclepias lanceolata, Asclepias purpurascens, Asclepias quadrifolia, Asclepias rubra, Asclepias speciosa, Asclepias syri-* aca, *Calendula arvensis, Calendula officinalis, Caltha leptosepala, Caltha natans, Caltha palustris, Chelidonium majus, Cichorium intybus, Coix* lacryma-jobi, *Delphinium staphisagria, Diospyros virginiana, Dipsacus fullonum, Dipsacus sativus, Drosera rotundifolia, Euphorbia hirta, Euphorbia lathyris, Euphorbia serpyllifolia, Ficus carica, Ficus palmata, Impatiens aurella, Impatiens balsamina, Impatiens capensis, Impatiens ecalcarata, Impatiens occidentalis, Impatiens parviflora, Juniperus sabina, Lactuca canadensis, Mercurialis annua, Mercurialis perennis, Monotropa uniflora, Ocimum* minimum, *Opuntia compressa, Paulownia tomentosa, Podophyllum peltatum, Ranunculus acris, Rhus diversiloba, Rhus typhina, Salvia lyrata, Sempervivum tectorum, Sonchus oleraceus, Symphoricarpos albus laevigatus, Taraxacum officinale, Zea mays* or mixtures thereof;

said substance with analgesic or anesthetic action is selected from extracts of *Aconitum carmichaelii, Aconitum ferox, Aconitum fischeri, Aconitum kusnezoffii, Aconitum lycoctonum, Aconitum uncinatum, Aconitum volubile, Arisaema thunbergii, Asarum heterotropoides, Asarum sieboldii, Capsicum frutescens, Coptis chinensis, Coptis teeta, Datura metel, Fritillaria sewerzowii, Gleditsia macracantha, Gleditsia triacanthos, Mentha arvensis, Mentha arvensis piperascens, Monarda menthifolia, Rhododendron molle, Salix pulchra, Tagetes lucida, Zanthoxylum bungeanum, Zanthoxylum schinifolium* or mixtures thereof.

12. A composition according to claim 10, wherein said substances with antivascular activity and/or helping the treatment of eliminating growths or warts and/or with analgesic or anesthetic action are contained in the composition in a percentage by weight between 0.01% and 10% by weight.

13. A composition according claim 1, for use in the treatment of Human papillomaviruses (HPV) cutaneous infections.

14. A composition for use according to claim 13, wherein said HPV cutaneous infection is a benign cutaneous infection, a common, plantar or flat wart, a papilloma, a condyloma, or the like.

15. A kit comprising an amount of the composition according to claim 1 for a single or multiple application, and a device for the mechanical removal of the lesion with abrasive mechanical properties.

\* \* \* \* \*